United States Patent [19]

Ponticello et al.

[11] Patent Number: 5,149,737

[45] Date of Patent: Sep. 22, 1992

[54] CARBOXY CONTAINING MONOMERS AND POLYMERS AND LATICES PREPARED FROM SAME

[75] Inventors: Ignazio S. Ponticello, Pittsford; Richard C. Sutton, Rochester, both of N.Y.

[73] Assignee: Eastman Kodak Company, Rochester, N.Y.

[21] Appl. No.: 654,112

[22] Filed: Feb. 12, 1991

Related U.S. Application Data

[63] Continuation-in-part of Ser. No. 539,768, Jun. 18, 1990, abandoned.

[51] Int. Cl.$^5$ .................. C08L 31/06; C08L 25/14; C08F 230/04; C08F 228/02; C08F 222/26
[52] U.S. Cl. .................. 524/564; 524/577; 526/240; 526/286; 526/324; 526/347; 526/307.2; 526/310; 526/326
[58] Field of Search .......................... 526/240

[56] References Cited

U.S. PATENT DOCUMENTS

| | | | |
|---|---|---|---|
| 3,616,229 | 10/1971 | Wildi et al. | 435/175 |
| 3,857,931 | 12/1974 | Hager | 436/509 |
| 4,101,549 | 7/1978 | Focella et al. | 436/533 |
| 4,138,383 | 2/1979 | Rembaum et al. | 524/809 |
| 4,140,662 | 2/1979 | Recket et al. | 436/533 |
| 4,181,636 | 1/1980 | Fischer | 525/54.1 |
| 4,235,867 | 11/1980 | Thoma | 436/531 |
| 4,264,766 | 4/1981 | Fischer | 536/51 |
| 4,352,884 | 10/1982 | Nakashima et al. | 435/180 |
| 4,574,130 | 3/1986 | Potter et al. | 523/111 |
| 4,634,651 | 1/1987 | Okawara et al. | 430/114 |
| 4,728,436 | 3/1988 | Kneller et al. | 210/701 |

*Primary Examiner*—Joseph L. Schofer
*Assistant Examiner*—Wu C. Cheng
*Attorney, Agent, or Firm*—James L. Tucker

[57] ABSTRACT

Certain ethylenically unsaturated polymerizable monomers having a reactive carboxy group are useful for preparing homo- and copolymers for a variety of uses, including diagnostic assays. The polymers can be supplied as latex particles in aqueous compositions. The monomers are represented by the structure:

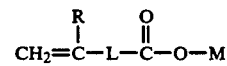

wherein:

R is hydrogen, halo or alkyl or 1 to 3 carbon atoms,
M is hydrogen, an alkali metal ion or an ammonium ion, and
L is a linking group having from 8 to 50 atoms in its linking chain, and comprises two or more divalent hydrocarbon groups connected or terminated with one or more nitrogen, oxygen or sulfur atoms, or with one or more groups containing such atoms in the linking chain, provided L has at least one arylene which is not directly connected to the terminal

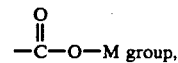

and further provided that none of the hydrocarbon groups has non-aromatic unsaturation.

12 Claims, No Drawings

CARBOXY CONTAINING MONOMERS AND POLYMERS AND LATICES PREPARED FROM SAME

RELATED APPLICATIONS

This is a continuation-in-part of U.S. Ser. No. 539,768, filed Jun. 18, 1990, now abandoned by ourselves.

Reference is made to copending and commonly assigned U.S. Ser. No. 539,774, filed on Jun. 18, 1990 by Sutton, Danielson, Findlay, Oakes, Oenick, Ponticello and Warren III and entitled "Biologically Active Reagents Prepared from Carboxy-Containing Polymer, Analytical Element and Methods of Use."

FIELD OF THE INVENTION

This invention relates to novel ethylenically unsaturated polymerizable monomers and to polymers prepared therefrom. Such polymers have a variety of uses, including their use in diagnostic methods and analytical elements which are described in more detail in U.S. Ser. No. 539,774, noted above.

BACKGROUND OF THE INVENTION

There is a continuing need in various research and industrial arts for ethylenically unsaturated polymerizable monomers which can be polymerized into useful polymers. For example, in the photographic arts, there is a need for layers in photographic elements which neutralize highly alkaline materials or which dissolve after a defined time to allow development or other chemical reactions. Such layers are often called "neutralizing" and "timing" layers. In other materials, there is a need for hardenable layers to immobilize various addenda or reactants. It is known in these arts to use polymers having reactive carboxy groups appended thereto. Typical polymers are those prepared from acrylic and methacrylic acids.

Moreover, there is also a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable, and suitable for automation or for use with test kits which can be readily used in doctor's offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses).

Methods in the art using the specific binding reactions generally require that one or more or both of the reactants be immobilized on a solid substrate of some type, so that unreacted (and generally water-soluble) materials can then be separated from the water-insoluble reaction product (often called a "complex"). In addition, such immobilized reactants can be used in affinity chromatography to remove a desired biologically active material from a mixture of such materials.

Biologically active substances have thus been immobilized to advantage on particulate substrates such as polymeric particles, animal and human erythrocytes, bacterial cells and other materials known in the art. In some cases, the particulate substrates are fashioned or chemically treated to provide reactive groups on their outer surfaces for appropriate reaction with the biological substance. If the particulate substrate is a polymeric material, it often can be prepared from monomers having the appropriate reactive groups.

For example, carboxylated latex particles have been used to prepare diagnostic reagents, as noted in U.S. Pat. No. 4,181,636 (issued Jan. 1, 1980 to Fischer). The described particles are prepared using a carboxyl-containing monomer such as acrylic acid, methacrylic acid, itaconic acid, aconitic acid, fumaric acid or maleic acid. Similar particles are described in U.S. Pat. No. 3,857,931 (issued Dec. 31, 1974 to Hager), U.S. Pat. No. 4,138,383 (issued Feb. 6, 1979 to Rembaum et al) and U.S. Pat. No. 4,264,766 (issued Apr. 28, 1981 to Fischer).

Two known monomers, 3-acrylamido-3-methylbutanoic acid and 2-acrylamido-2-hydroxyacetic acid, have been polymerized to form polymers. These monomers are generally water-soluble and are difficult to copolymerize with oleophilic monomers and are not readily polymerized to form monodisperse particles. For example, U.S. Pat. No. 4,728,436 (issued Mar. 1, 1988, to Kneller et al) describes water-soluble polymers for use as scale inhibitors in industrial water.

U.S. Pat. No. 4,634,651 (issued Jan. 6, 1987 to Okawara et al) describes crosslinked resins useful in liquid developers for electrostatic photography. The resins have electric charge due to the presence of carboxy groups within the crosslinked resin matrix. The polymers used to prepare the resins are prepared in organic solvents.

In U.S. Pat. No. 4,574,130 (issued Mar. 4, 1986, to Potter et al), there are disclosed ethylenically unsaturated polymerizable monomers which are precursors to polymers useful as surfactants in medical or surgical adhesives. These polymers are highly water-soluble and not suitable for forming small particles. Moreover, such polymers generally have low glass transition temperatures.

Another advance in the art relates to the use of specific compounds to attach biological materials to particulate substrates having reactive carboxy groups. Generally, water-soluble carbodiimides have been used, as described in the references noted above. More recently, however, carbamoylonium compounds have been used for this purpose with considerable advantages, as described in U.S. Ser. No. 373,304 (filed Jun. 29, 1989 by Sutton et al) as a CIP of U.S. Ser. No. 286,097 (filed Dec. 19, 1988) which is a CIP of U.S. Ser. No. 098,429 (filed Sep. 18, 1987).

The modification of protein adsorption on polymeric surface has been a common goal for many workers trying to apply polymer technology to in vivo and in vitro uses in biotechnology. Undesirable protein adsorption has been a continual problem. For example, nonspecific adsorption is a major concern in the use of polymers for affinity chromatography for the purification of proteins.

The modification of polymer surfaces has taken many forms, including physical coatings, graft copolymerization, chemical treatments and plasma gas discharge treatment. The hydrophilic nature of the polymer surface has been the subject of considerable debate and research because an increase in hydrophilicity reduces adsorption of some proteins, but not others. As noted in the art cited above, the use of reactive side chains has also received considerable attention in the art.

There is a need in the art to find new polymerizable monomers and water-insoluble polymers prepared therefrom which show improvement over the standard carboxy-containing polymers, especially in copolymerization efficiency and in the attachment of biological materials for use in research and various analytical and diagnostic procedures.

SUMMARY OF THE INVENTION

The needs in the art noted above are met with a compound having a reactive carboxy group, or salt thereof, which is represented by the structure:

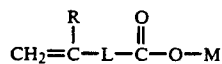

wherein:
R is hydrogen, halo or alkyl of 1 to 3 carbon atoms,
M is hydrogen, an alkali metal ion or an ammonium ion, and
L is a linking group having from 8 to 50 atoms in its linking chain, and comprises two or more divalent hydrocarbon groups connected or terminated with one or more nitrogen, oxygen or sulfur atoms, or with one or more groups containing such atoms in the linking chain, provided L has at least one arylene which is not directly connected to the terminal

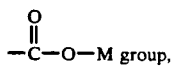

and further provided that none of the hydrocarbon groups has non-aromatic unsaturation.

This compound is used to prepare a homopolymer, or a polymer having recurring units derived from:

(a) from 80 to about 99.8 mole percent of one or more ethylenically unsaturated polymerizable, non-crosslinkable, vinyl aromatic monomers which provide hydrophobicity to the polymer, (b) from about 0.2 to 20 mole percent of one or more ethylenically unsaturated polymerizable monomers represented by the structure:

wherein:
R is hydrogen, halo or alkyl of 1 to 3 carbon atoms,
M is hydrogen, an alkali metal ion or an ammonium ion, and
L is a linking group having from 8 to 50 atoms in its linking chain, and comprises two or more divalent hydrocarbon groups connected or terminated with one or more nitrogen, oxygen or sulfur atoms, or with one or more groups containing such atoms in the linking chain, provided L has at least one arylene which is not directly connected to the terminal

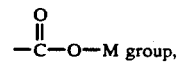

and further provided that none of the hydrocarbon groups has non-aromatic unsaturation, and (c) from 0 to about 15 mole percent of one or more additional ethylenically unsaturated polymerizable monomers other than those identified in categories (a) and (b) above.

These polymers are useful for the preparation of biologically active reagents, and in a variety of analytical and diagnostic procedures, including the analytical elements and methods described in more detail in U.S. Ser. No. 539,774 (of Ponticello et al, noted above). The reagents can also be used in affinity chromatography, as described in the noted copending application.

An aqueous latex composition of this invention comprises particles having, on at least the outer surface thereof, the water-insoluble homopolymer or copolymer described above, the particles being present at from about 0.5 to about 50 weight percent of the composition.

The advantages of the polymers of this invention resides in the fact that the carboxy group is extended from the polymer surface by a sufficient length to allow improved results in the attachment of biologically active substances and their subsequent use. Thus, in the structure noted above, the organic group identified as "L" is critically from 8 to 50 carbon, nitrogen, oxygen or sulfur atoms in chain length. The extended linking group enables the carboxy groups to be more easily activated by carbodiimides or other activation agents when proteins are attached to, or gelatin is grafted to, the particles.

The extended hydrophilic carboxy group on the monomers of this invention provide certain advantages over monomers having shorter carboxy groups which are known in the art. During emulsion polymerization, the monomers of this invention have less tendency to polymerize in the aqueous phase as solution (or water-soluble) polymers. Thus, our novel monomers are more easily and more completely incorporated into water-insoluble latex particles, and thereby facilitate attachment of proteins or other biological compounds. Latices prepared from acrylic acid contain unwanted soluble polymer in the aqueous phase, which for some uses, must be removed at considerable expense. The monomers of this invention produce less water-soluble polymer.

Further, the reactivity ratios of the monomers of this invention are more favorable than known carboxy-containing monomers for polymerization with aromatic monomers (such as styrene or styrene derivatives). This advantage is possible because of the presence of aromatic groups in the linking group of the monomers, and the use of styrene comonomers (styrene derivatives).

DETAILED DESCRIPTION OF THE INVENTION

The monomers of this invention can be used to prepare homopolymers and copolymers used in a number of industrial and commercial contexts. For example, the resulting polymers can be used as photographic timing layers, the function of which is known in the art, including U.S. Pat. No. 4,061,496 (issued Dec. 6, 1977 to Hannie et al) and U.S. Pat. No. 4,375,506 (issued Mar. 1, 1983 to Abel et al). They can also be used as photographic neutralizing layers, the function of which is described for example in *Research Disclosure* 12331 (published July, 1974) and U.S. Pat. No. 3,362,819 (issued Jan. 9, 1968 to Land). *Research Disclosure* is a publication available from Kenneth Mason Publications, Ltd., The Old Harbourmaster's, 8 North Street, Emsworth, Hampshire P010 7dd, England.

Polymers of this invention can also be used in forming particles used to produce gel-grafted beads which are then used to provide gel-grafted matte bead layers in photographic elements, for example as in U.S. Pat. No. 4,855,219 (issued Aug. 8, 1989 to Bagchi et al). Other photographic uses of such polymers are also known.

Preferably, the polymers of this invention are used to provide reagents for medical, analytical or diagnostic methods, as described in more detail in the copending U.S. Ser. No. 539,774 (Ponticello et al, noted above). Compounds of biological interest can be attached to the polymers through the available carboxy groups using a variety of activating agents such as carbodiimides, dication ethers or carbamoylonium compounds, all of which are known in the art. Because the carboxylic acid group is on an extended hydrophobic chain in the present invention, however, the polymers of this invention provide advantages over known polymers for the same use (as noted above).

The polymers of this invention have as an essential component recurring units derived from one or more ethylenically unsaturated polymerizable monomers having the following structure:

wherein R is hydrogen, halo or alkyl of 1 to 3 carbon atoms, M is hydrogen, an alkali metal ion or an ammonium ion and L is as described below. A mixture of monomers can be used if desired, although preferably only one such monomer is used to prepare each copolymer.

More specifically, in the structure noted above, R is hydrogen, halo (such as chloro or bromo) or alkyl of 1 to 3 carbon atoms (such as methyl, ethyl, isopropyl and n-propyl). More preferably, R is hydrogen or methyl.

Also, M is hydrogen, an alkali metal ion (such as lithium, sodium and potassium) or an ammonium ion (such as ammonium, tetramethylammonium and tetraethylammonium). Preferably, M is hydrogen or an alkali metal ion, and more preferably, it is hydrogen or sodium.

L is a linking group which has from 8 to 50 of a combination of carbon, nitrogen, oxygen or sulfur atoms in the linking chain. The linkage comprises two or more divalent hydrocarbon groups, such as alkylene, arylene, alkylenearylene, and arylenealkylene groups, which are connected or terminated with the noted heteroatoms or with heteroatom-containing groups such as carbonyl, sulfonyl, imino and others known in the art.

L also has at least one arylene group (defined below) in the linking chain which is not directly connected to (that is, bounded directly to) the terminal

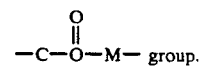

Thus, L can have more than one arylene group anywhere in the chain, but if there is only one arylene group in the chain, it cannot be directly connected to the terminal group. None of the hydrocarbon groups has non-aromatic unsaturation (that is, alkenylene or alkynylene moieties). The only unsaturation present in the hydrocarbon groups is in the arylene groups.

Such hydrocarbon groups can have from 1 to 12 carbon atoms (such as methylene, trimethylene, hexylene, isopropylene, n-octylene, dodecylene, chlorophenylene, bromophenylene, phenylene, tolylene, xylylene, naphthylene, p-methylenephenylene, trimethylenephenylenemethylene and others readily apparent to one skilled in the art), and can be branched, linear or cyclical, substituted or unsubstituted with one or more alkyl groups (preferably of from 1 to 12 carbon atoms, such as methyl, ethyl, isopropyl, hexyl and octyl), alkoxy (preferably from 1 to 12 carbon atoms, such as methoxy, ethoxy, propoxy, t-butoxy and octyloxy), cycloalkyl (preferably from 4 to 6 carbon atoms, such as cyclobutyl, cyclohexyl and cyclopentyl), aryl (preferably from 6 to 12 carbon atoms, such as phenyl, tolyl, xylyl, naphthyl, 4-methoxyphenyl and chlorophenyl). Such groups are not difficult to design or synthesize for one skilled in synthetic chemistry.

Preferably, the hydrocarbon groups are connected or terminated with an oxy, thio, imino (—NR$^1$—), carbonyloxy (—COO—), carbonylimino (—CONR$^1$—), ureylene (—NR$^1$CONR$^1$—) or sulfonylimino (—SO$_2$NR$^1$—) group, wherein each R$^1$ in the noted groups is independently hydrogen, alkyl having 1 to 10 carbon atoms (such as methyl, ethyl, isopropyl, n-butyl, hexyl, benzyl and 2,4-dimethylpentyl), cycloalkyl having 4 to 10 carbon atoms in the backbone (such as cyclopentyl, cyclohexyl and 1,3-dimethylcylohexyl) or aryl having 6 to 14 carbon atoms in the backbone (such as phenyl, xylyl, p-chlorophenyl, naphthyl and anthryl). R$^1$ also does not contain non-aromatic unsaturation.

Representative L groups include, but are not limited to: p-phenylenemethyleneoxycarbonyltrimethylene, carbonyloxy-p-phenylene-ureylenepentamethylene, p-phenylenemethylenethioethyleneoxycarbonyltrimethylene, p-phenylenemethyleneiminocarbonyltrimethylene, p-phenylenemethyleneiminocarbonyltrimethylene, p-phenylene(methyl)iminoethyleneoxycarbonyltrimethylene, p-phenylenemethylenethioethylene, p-phenylenemethylenethioethyleneiminocarbonylmethyleneoxymethylene, p-phenylenemethylenethioethyleneiminocarbonylmethylenethiomethylene, p-phenylenemethylenethioethyleneiminocarbonyltrimethylene, p-phenylenemethylenethio-1-carboxyethylene, p-phenylenemethylenethio-p-phenylene, p-phenylene-methylenethioethyleneoxyethylenethiomethyleneoxy-carbonylethylene, p-phenylenemethyleneoxy-p-phenylenemethylenethioethylene, p-phenylenemethylenethioethyleneoxyethylenethioethyleneoxycarbonylethylene, p-phenylenemethyleneoxy-p-phenylenemethylenethio-p-phenylenemethylenethiotrimethylene and p-phenylenemethylenethioethyleneoxyethylenethioethyleneoxycarbonyl-p-phenylene.

Representative monomers of the present invention described by the structure identified above include, but are not limited to: mono-m and p-vinylbenzyl glutarate, mono-p-vinylbenzyl glutarate, 4-(4-carboxybutyramido)styrene, mono-2-(p-vinylbenzylthio)ethyl glutarate, mono-2-(m-and p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)-succinic acid, 2-(4-vinylbenzylthio)benzoic acid, mono-2-[2-(4-vinylbenzylthio)ethoxy]ethylthiomethyl malonate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio]benzylthio}butyric acid.

The most preferred monomer is 3-(p-vinylbenzylthio)propionic acid.

While the monomers described above can be polymerized to form homopolymers, preferably they are used to prepare copolymers with one or more additional ethylenically unsaturated polymerizable monomers. For instance, the oleophilic monomers identified above as (a) monomers are useful for providing hydrophobicity or water-insoluble properties to the resulting copolymer. A mixture of such monomers can be used if desired. Such monomers would include, but not be limited to, non-crosslinkable vinyl aromatics, such as styrene and styrene derivatives such as 4-vinyltoluene, α-methylstyrene, 2,5-dimethylstyrene, 4-t-butylstyrene, m and p-chloromethylstyrene, p-hydroxystyrene, 2,5-dimethoxystyrene, 3,4-dimethoxystyrene, 3,4-methylenedioxystyrene and 2-chlorostyrene. Crosslinkable monomers are specifically excluded. Other useful vinyl aromatic monomers would be readily apparent to one skilled in polymer chemistry.

In addition, ethylenically unsaturated polymerizable monomers (c) other than those described above for monomers (a) or (b) can be copolymerized in minor amounts to provide desirable properties. For example, such monomers include anionic monomers containing sulfonic acid groups or salts thereof, including 2-acrylamido-2-methylpropane sulfonic acid, 3-methacryloyloxypropane-1-sulfonic acid, p-styrene sulfonic acid and salts thereof, and others readily apparent to one skilled in the art. Also included in the (c) group of monomers are nonionic monomers such as acrylamide, methacrylamide, N-isopropylacrylamide, 2-hydroxyethyl acrylate, vinyl acetate, vinylidene chloride, vinyl bromide, acrylonitrile, N-vinyl-2-pyrrolidone and others readily apparent to one skilled in the art as long as the resulting copolymer is highly hydrophobic and can be formed as water-insoluble particles. A skilled polymer chemist would be able to readily fashion useful polymers from hundreds of available or producible monomers using the teaching present herein.

Preferably, the copolymers of this invention are composed of recurring units derived from about 85 to about 99.5 mole % of (a), from about 0.5 to about 15 mole % of (b), and from 0 to about 10 mole % of (c).

The copolymers of this invention are prepared using standard emulsion or suspension polymerization techniques, as described for example by Sorenson et al in *Preparative Methods of Polymer Science*, 2nd Ed. (1968), Wiley and Sons, New York, and by Stevens, *Polymer Chemistry, An Introduction*, Addison Wesley Publishing Co., London, 1975, although there are certain preferred conditions which are discussed below.

Suspension polymerization procedures are well known and generally involve mechanically dispersing the monomers in a liquid, usually water, and polymerizing the monomer droplets formed from the dispersing action. Polymerization initiators which are soluble in the monomer are generally used, and surfactants can also be used. Small particles of polymer are obtained with careful control of the polymerization conditions, which particles can be isolated using filtration, centrifugation or spray drying.

The polymers of this invention are preferably prepared using emulsion polymerization techniques. In emulsion polymerization (whether batch, continuous or semi-continuous modes as known in the art), it is highly preferred that the copolymers be prepared as small particles without the use of surfactants (also known as emulsifiers) or colloidal dispersing agents because residual surfactant on the particles tend to interfere with attachment of biologically active substances (for example, antibodies and enzymes). Thus, the resulting latex is substantially free of surfactants and colloidal dispersing agents. Conditions for surfactant-free polymerization is known in the art, for example as described in U.S. Pat. No. 4,415,700 (noted above) and *Research Disclosure* publication 15963 (July, 1977), both incorporated herein by reference. Research Disclosure is a publication available from Kenneth Mason Publications, Ltd., The Old Harbourmaster's, 8 North Street, Emsworth, Hampshire P010 7DD, England. Continuous polymerization is the most preferred technique whereby monomers are added to a reaction vessel over a period of time, as described in more detail in the noted *Research Disclosure* publication.

Some general conditions for emulsion polymerization include reaction of the monomers in the presence of water-soluble, free radical polymerization initiators (such as redox combinations of persulfates and bisulfites including potassium persulfate, ammonium persulfate, potassium bisulfite and sodium bisulfite and others known in the art) in an amount of from about 0.1 to about 5 weight % over a period of from about 30 to about 1200 minutes at a temperature of from about 30° to about 95° C. Other conditions include the use of chain transfer agents such as dodecanethiol at concentrations of from about 0.05 to about 5% (based on monomer weight).

Representative preparations of copolymers useful in this invention are provided in Examples 29–58 below.

Copolymers of this invention are generally in small particulate form (latices, predominantly spherical) having an average diameter of from about 0.01 to about 20 μm. Preferably, the particles have an average diameter of from about 0.05 to about 10 μm, and more preferably from about 0.1 to about 5 μm. The water-insoluble particles are generally nonporous and nonswellable in water or water-miscible solvents (such as alcohols), but they are also generally water-dispersible due to their small size. Polymerization generally results in from about 0.5 to about 50 percent solids of copolymer, although, the latex composition of this invention generally has from about 0.5 to about 25 (preferably from about 1 to about 20) percent solids of copolymer particles when used.

Representative homo- and copolymers of this invention include, but are not limited to:
poly(mono-m and p-vinylbenzyl glutarate),
poly[styrene-co-mono-2-(m and p-vinylbenzylthio)ethyl glutarate] (98.3:1.7 molar ratio),
poly[styrene-co-2-(4-vinylbenzylthio)succinic acid] (97.98:2.02 molar ratio),
poly[styrene-co-2-(4-vinylbenzylthio)benzoic acid] (97.75:2.25 molar ratio),
poly{{styrene-co-mono-2-{2-[2-(4-vinylbenzylthio)ethoxy]ethylthio}ethyl succinate}} (98.64:1.36 molar ratio),
poly{{styrene-co-mono-2-{2-[2-(4-vinylbenzylthio)ethoxy]ethylthio}ethyl phthalate}} (98.79:1.21 molar ratio),
poly(styrene-co-mono-m and p-vinylbenzyl glutarate) (97.84:2.16 molar ratio),
poly[styrene-co-mono-2-(p-vinylbenzylthio)ethyl glutarate] (98.25:1.75 molar ratio),
poly[styrene-co-3-(p-vinylbenzylthio)propionic acid] (97.59:2.41 and 95.2:4.8 molar ratios),
poly[styrene-co-mono-2-(4-vinylbenzylthio)ethyl succinate] (98.17:1.83 molar ratio),
poly{styrene-co-4-[2-(carboxymethoxyacetoxy)ethylthiomethyl]styrene} (98.26:1.74 molar ratio),
poly(styrene-co-mono-4-vinylbenzyl succinate) (97.71:2.29 molar ratio),
poly[styrene-co-3-p-(vinylbenzylthio)propionic acid] (95.2:4.8), and
poly[styrene-co-3-(p-vinylbenzylthio)propionic acid-co-2-hydroxyethyl acrylate] (92.6:2.4:5 molar ratio).

While in most cases, the polymers of this invention are homogeneous particles, that is, the particles are composed of the same polymer throughout, it is essential that at least the outer surface of polymeric particles be composed of a polymer of this invention. Particles having an outer shell of the polymer can be prepared by graft copolymerization or other known procedures whereby an already formed particle is coated with another polymer.

In one embodiment, the polymers of this invention can be used to prepare what are known in the art as core-shell polymer particles. In these materials, the core is prepared from a polymer different from the shell polymer. For example, the core can be any water-insoluble vinyl addition polymer latex particle. The shell of the particles could be prepared from the polymers of this invention while the core is prepared from a different polymer. Methods of making core-shell polymer particles are well known in the art, for example U.S. Pat. No. 4,401,765 (issued Aug. 30, 1983 to Craig et al) and U.S. Ser. No. 098,583 (filed Sep. 18, 1987 by Sutton et al). Generally, the shell polymer comprises from about 20 to about 70, and preferably from about 30 to about 60, weight percent of the total core-shell weight. Core-shell particles can be used in agglutination assays for diagnostic purposes.

Generally, core-shell polymers are prepared using staged emulsion polymerization procedures. For example, emulsion polymerization of the core is carried to substantial completion by continuously adding reactants to a reaction vessel under standard conditions. Monomers and catalysts needed to make the shell polymer are then continuously added to the vessel containing the latex of the core polymer. In this manner, the shell has a definite known composition rather than being a mixture of core and shell monomers. Representative details of preparations are provided in U.S. Ser. No. 098,583 (noted above).

The following examples are provided to illustrate, and not to limit, the scope of this invention. The starting materials are commercially available unless otherwise noted. All percentages are by weight unless otherwise indicated.

EXAMPLE 1

Preparation of Mono-p-vinylbenzyl Glutarate

To a solution of p-vinylbenzyl alcohol (76 g, 0.56 mole) and glutaric anhydride (70 g, 0.61 mole) in chloroform (600 ml) was added dimethylaminopyridine (75 g, 0.61 mole) in chloroform (250 ml) in dropwise fashion at room temperature over 15 minutes. Heat was evolved with the temperature rising to 45° C. The reaction mixture was stirred for an additional hour at ambient temperature. It was then washed three times with hydrochloric acid (5%, 200 ml) and twice with saturated sodium chloride (250 ml), dried over anhydrous magnesium sulfate, filtered and the solvent removed to provide the crude acid (130 g, 94% yield). A small sample was chromatographed to provide pure monomer. Analysis calculated for $C_{14}H_{16}O_4$: C, 67.73, H, 6.50, Found: C, 66.82, H, 6.42.

Nuclear magnetic resonance data: $(CDCl_3)_{TMS}$ w 1.90 (m, 2H, $—CH_2—\underline{CH_2}—CH_2—$), 2.40 (m, 4H, $—\underline{CH_2}—CH_2—\underline{CH_2}—$), 5.10 (s, 2H, $\underline{CH_2}O$), 5.20 (dd, 1H, Ha), 5.75 (dd, 1H, Hb), 6.7 (dd, 1H, Hc), 7.35 (dd, 4H, phenyl H), confirmed the structure of the desired monomer.

A repeat of this preparatory method recrystallized from ethyl ether/petroleum ether (3:1), was chromatographed on acid washed aluminum oxide to give pure material at a m.p. of 44°-48° C.

EXAMPLE 2

Preparation of mono-4-Vinylbenzyl succinate

This compound was prepared by procedures analogous to those of Example 1 except substituting succinic anhydride for the glutaric anhydride: m.p. of 85.5°-87.5° C. Yield of 75%. Analysis calculated for $C_{13}H_{14}O_4$: C, 66.66, H, 6.02. Found: C, 66.54, H, 6.05. $^1H$ NMR $(CDCl_3)$ δ

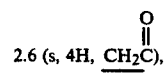

2.6 (s, 4H, $\underline{CH_2}C$), 5.0 (s, 2H, $\underline{CH_2}O$) 5.15+5.7 (AB quartet, 2H, $\underline{CH_2}=$), 6.65 (m, 1H, $\underline{CH}=$), 7.3 (m, 4H, ArH's).

EXAMPLE 3

Preparation of the Intermediate, p-Vinylbenzyl 2-Hydroxyethyl Sulfide

To a solution of potassium hydroxide (86 g, 1.3 moles) and 2,6-di-tert-butyl-p-cresol (1 g) in ethanol (1 liter) at room temperature was added under nitrogen atmosphere 2-mercaptoethanol (100 g, 1.3 moles), over fifteen minutes. Following addition the solution was stirred an additional hour at room temperature and then p-vinylbenzyl chloride (198 g, 1.3 moles) was added at room temperature over one hour. After addition, the mixture was allowed to reach ambient temperature overnight. The mixture was filtered and the solvent removed on a rotary evaporator. To the residue was added dichloromethane (1.2 liter) and the solvent was washed with water (3×200 ml), then with saturated NaCl solution (200 ml), dried over anhydrous magnesium sulfate, filtered and the solvent removed on a rotary evaporator. To the residue was added diethyl ether (200 ml) and petroleum ether (800 ml). The product crystallized and was then filtered to give a white solid: m.p. of 44°–45.5° C. Yield of 85%. Analysis calculated for $C_{11}H_{14}OS$: C, 68.0, H, 7.26, S, 16.50. Found: C, 67.7, H, 6.98, S, 15.37.

EXAMPLE 4

Preparation of mono-2-(p-Vinylbenzylthio)ethyl Glutarate

To a mixture of chloroform (400 ml), p-vinylbenzyl 2-hydroxyethyl sulfide (48.5 g, 0.25 moles) prepared in Example 2 and glutaric anhydride (36.6 g, 0.3 mole) and added under a nitrogen atmosphere a solution of N,N-dimethylaminopyridine (36.6 g, 0.30 moles) in chloroform (200 ml) over 5 minutes at ambient temperature. Shortly after the addition, the reaction temperature rose to about 40° C. The reaction was at ambient temperature overnight. The mixture was then washed with 5% hydrochloric acid (2×100 ml), saturated NaCl (100 ml), dried over anhydrous magnesium sulfate, filtered and the solvent removed on a rotary evaporator to give a residual oil that was not further purified. The compound had a m.p. of 55°–57° C. Yield 66%. 1H NMR $CDCl_3$ δ1.9 (m, 2H, —C—$\underline{CH_2}$—C—),

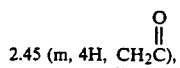
2.45 (m, 4H, $\underline{CH_2}$C), 2.6 (t, 2H, $\underline{CH_2}$—S), 3.67 (s, 2H, $\underline{ArCH_2}$—S),

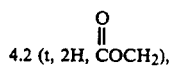
4.2 (t, 2H, $\underline{COCH_2}$), 5.15+6.7 (AB quartet, 2H, $\underline{CH_2}$=), 6.65 (m, 1H, $\underline{CH}$=), 7.3 (m, 4H, ArH's).

EXAMPLE 5

Preparation of mono-2-(4-Vinylbenzylthio)ethyl succinate

This compound was prepared by procedures analogous to those of Example 4 except substituting succinic anhydride for glutaric anhydride. Analysis calculated for $C_{15}H_{18}O_4S$: C, 61.20, H, 6.16, S, 10.89. Found: C, 61.48, H, 6.20, S, 9.52. 1H NMR ($CDCl_3$) δ

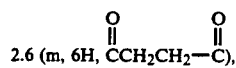
2.6 (m, 6H, $\underline{CCH_2CH_2}$—C), $CH_2$—S), 3.7 (s, 2H, Ar—$CH_2$—S—C),

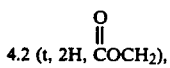
4.2 (t, 2H, $\underline{COCH_2}$), 5.15+5.7 (AB quartet, 2H, $\underline{CH_2}$=), 6.7 (m, 1H, $\underline{CH}$=) 7.3 (m, 4H, ArH's).

EXAMPLE 6

Preparation of 4-[2-(Carboxymethoxyacetoxy)ethylthiomethyl]styrene

This compound was prepared by procedures analogous to those of Example 5 except substituting diglycolic anhydride for glutaric anhydride: m.p. of 63°–68° C. Yield of 77%. Analysis calculated for $C_{15}H_{18}O_5S$: C, 58.85, H, 5.85, S, 10.33. Found: C, 58.90, H, 5.77, S, 9.24. 1H NMR ($CDCl_3$) δ2.58 (t, 2H, $\underline{CH_2}$—S), 3.65 (s, 2H, Ar—$\underline{CH_2}$—S—C),

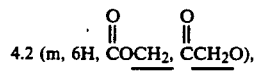
4.2 (m, 6H, $\underline{COCH_2}$, $\underline{CCH_2O}$), 5.15+5.65 (AB quartet, 2H, $\underline{CH_2}$=), 6.65 (m, 1H, $\underline{CH}$=), 7.25 (m, 4H, ArH's), 10.6 (s, 1H, $\underline{COOH}$).

EXAMPLE 7

Preparation of 4-(4-Carboxybutyramido)methyl)styrene

This compound was prepared by procedures analogous to those of Example 1 except substituting p-vinylbenzylamine for vinylbenzyl alcohol used in Example 1: m.p. of 132°–133° C. Yield of 80%. Analysis calculated for $C_{14}H_{17}NO_3$: C, 68.0, H, 6.93, N, 5.66. Found: C, 67.67, H, 6.85, N, 5.57. 1H NMR ($DMSOd_6$) δ1.7 (m, 2H, C—$\underline{CH_2}$—C),

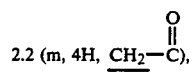
2.2 (m, 4H, $\underline{CH_2}$—C), 4.25 (d, 2H, $\underline{CH_2}$—N), 5.15+5.7 (AB quartet, 2H, $\underline{CH_2}$=), 6.7 (m, 1H $\underline{CH}$=), 7.3 (AB quartet, 4H, ArH's), 83. (broad t, 1H, $\underline{NH}$).

EXAMPLE 8

Preparation of 3-(p-Vinylbenzylthio)propionic acid

To a solution of potassium hydroxide (84 g, 1.3 moles) and 2,6-di-tert-butyl-p-cresol (1 g) in ethanol (1.2 liter) at room temperature was added under a nitrogen atmosphere 3-mercaptopropionic acid (65.0 g, 0.61 mole) over 10 minutes. Following addition the solution was stirred an additional hour at room temperature and then p-vinylbenzyl chloride (93 g, 0.6 mole) was added at room temperature over 30 minutes. After addition, the solution was stirred at ambient temperature overnight. The next day the mixture was poured into ice and concentrated hydrochloric acid (150 ml). The solid was filtered and dried on a funnel under vacuum. The solid was dissolved in dichloromethane (1.4 liter), washed with saturated NaCl (200 ml), dried over anhydrous magnesium sulfate, filtered and the solvent removed on a rotary evaporator. The residue was dissolved in diethyl ether (600 ml), hexane (1 liter) was added to the cloud point, and then the mixture was placed in a freezer. The white solid product was collected by filtration: m.p. of 77°–78° C. Yield of 80%. Analysis calculated for $C_{12}H_{14}O_2S$: C, 64.84, H, 6.35, S, 14.42. Found: C, 64.98, H, 6.29, S, 14.02. 1H NMR ($CDCl_3$) δ2.6 (m, 4H, $\underline{CH_2CH_2}$), 3.7 (s, 2H, $\underline{ArCH_2S}$), 5.15+5.65 (AB quartet, 2H, $\underline{CH_2}$=), 6.65 (m, 1H, $\underline{CH}$=), 7.3 (m, 4H, ArH's).

EXAMPLE 9

Preparation of 2-(4-Vinylbenzylthio)succinic acid

This compound was prepared by procedures analogous to those of Example 8 except substituting 2-mercaptosuccinic acid for the 3-mercaptopropionic acid: m.p. of 173°-175° C. Yield of 80%. Analysis calculated for $C_{13}H_{14}O_4S$: C, 58.63, H, 5.30, S, 12.04. Found: C, 58.62, H, 5.29, S, 11.68. 1H NMR (DMSOd$_6$) δ2.7 (m, 2H, C$\underline{H_2}$—CO$_2$H), 3.5 (m, 1H, S—C$\underline{H}$—CO$_2$H), 3.9 (s, 2H, C$\underline{H_2}$S), 5.2+5.75 (AB quartet, 2H, C$\underline{H_2}$=), 6.7 (m, 1H, C$\underline{H}$=), 7.4 (m, 4H, ArH's).

EXAMPLE 10

Preparation of 2-(4-Vinylbenzylthio)benzoic acid

This compound was prepared by the procedures of Example 8 except using o-mercaptobenzoic acid in place of 3-mercaptopropionic acid: m.p. of 207°-209° C. Yield of 70%. Analysis calculated for $C_{16}H_{14}O_2S$: C, 71.08, H, 5.22, S, 11.86. Found: C, 70.41, H, 5.15, S, 11.39. $^1$H NMR (DMSOd$_6$) δ4.1 (s, 2H, C$\underline{H_2}$—S), 5.15+5.73 (AB quartet, 2H, C$\underline{H_2}$=), 6.68 (m, 1H, C$\underline{H}$=), 7.0-8.0 (m, 8H, ArH's).

EXAMPLE 11

Preparation of 4-[2-(4-Carboxybutyramido)ethylthiomethyl]styrene

This compound was prepared by procedures analogous to those of Example 1, except substituting p-vinylbenzyl 2-aminoethyl sulfide for the p-vinylbenzyl alcohol. m.p. of 118°-119° C. Yield of 70% of white solid. Analysis calculated for $C_{16}H_{21}NO_3S$: C, 62.51, H, 6.89, N, 4.56. Found: C, 62.25, H, 6.84, N, 4.42. 1H NMR (DMSOd$_6$) δ1.7 (m, 2H, C—C$\underline{H_2}$—C),

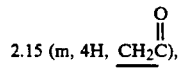
2.15 (m, 4H, C$\underline{H_2}$C), 2.45 (t, 2H, C$\underline{H_2}$—S), 3.2 (m, 2H, C$\underline{H_2}$N), 3.7 (s, 2H, ArC$\underline{H_2}$S), 5.15+5.75 (AB quartet, 2H, C$\underline{H_2}$=), 6.7 (m, 1H, C$\underline{H}$=), 7.3 (m, 4H, ArH's), 7.8 (broad t, 1H, NH).

EXAMPLE 12

Preparation of 4-[2-(Carboxymethoxyacetamido)ethylthiomethyl]styrene

This compound was prepared by procedures analogous to those of Example 11 except substituting diglycolic acid anhydride in place of the glutaric anhydride: m.p. of 44.5°-46° C. Yield of 80% of white solid. Analysis calculated for $C_{15}H_{19}NO_4S$: C, 58.23, H, 6.19, N, 4.53. Found: C, 57.66, H, 6.20, N, 4.43. 1H NMR (CDCl$_3$) δ2.5 (t, 2H, CH$_2$S), 3.4 (m, 2H, C$\underline{H_2}$N), 3.65 (s, 2H, ArC$\underline{H_2}$S),

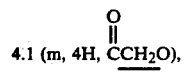
4.1 (m, 4H, CCH$_2$O), 5.15+5.65 (AB quartet, 2H, CH$_2$=), 6.65 (m, 1H, C$\underline{H}$=), 7.3 (m, 4H, ArH) 7.5 (broad s, 1H, NH).

EXAMPLE 13

Preparation of 4-[2-(Carboxymethylthioacetamido)ethylthiomethyl]styrene

This compound was prepared by procedures analogous to those of Example 11 except substituting thiodiglycolic acid anhydride for the glutaric anhydride: mp. of 97°-99° C. Yield of 80% of white solid. Analysis calculated for $C_{15}H_{19}NO_3S_2$: C, 55.36, H, 5.85, N, 4.30, S, 19.7. Found: C, 54.70, H, 5.66, N, 4.29, S, 19.8. 1H NMR (CDCl$_3$) δ2.5 (t, 2H, C$\underline{H_2}$S),

3.3 (m, 6H, C$\underline{H_2}$N, $\underline{C}$CH$_2$—S), 3.65 (s, 2H, ArC$\underline{H_2}$S), 5.15+5.65 (AB quartet, 2H, CH$_2$=), 6.6 (m, 1H, C$\underline{H}$=), 7.3 (m, 5H, ArH's+N$\underline{H}$), 9.0 (s, 1H, CO$_2$H).

EXAMPLE 14

Preparation of 2-{2-[2-(4-vinylbenzylthio)ethoxy]ethylthio}ethanol

To a solution of potassium hydroxide (48 g, 0.72 molar) in ethanol (1 liter) was added bis(2-mercaptoethyl)ether (100 g, 0.72 moles) and the mixture was stirred for 30 minutes at ambient temperature. Then 2-bromoethanol (90 g, 0.72 mole) was added to the mixture all at once and stirring was continued at ambient temperature for 30 minutes, then potassium hydroxide (48.0 g, 0.72 mole) was added to the mixture and again stirring was continued at ambient temperature for 30 minutes. p-Vinylbenzyl chloride (110 g, 0.72 mole) was then added all at once and stirred at room temperature for 16 hours. The next day the reaction was filtered and the solvent removed on a rotary evaporator. To the residue was added dichloromethane (1.2 liter), the mixture was washed with water (200 ml), 5% hydrochloric acid (200 ml), saturated sodium chloride (200 ml) then dried over anhydrous magnesium sulfate, filtered and the solvent removed in a rotary evaporator. To the residue was added diethyl ether (350 ml) and hexane (200 ml) and then the mixture was cooled in the freezer, filtered to give a white solid (94 g). Chromotography of the mother liquors gave additional product (48 g). Yield of 66%. Analysis calculated for $C_{15}H_{22}O_2S_2$. C, 60.36, H, 7.43, S, 21.49. Found: C, 60.41, H, 7.43, S, 21.14. $^1$H NMR (CDCl$_3$) δ2.7 (m, 6H, C$\underline{H_2}$S—CH$_2$+SCH$_2$), 3.0-3.8 (m, 9H, ArC$\underline{H_2}$S, C$\underline{H_2}$OCH$_2$, C$\underline{H_2}$OH), 5.15+5.65 (AB quartet, 2H, C$\underline{H_2}$=), 6.68 (m, 1H, C$\underline{H}$=), 7.25 (m, 4H, ArH's).

EXAMPLE 15

Preparation of mono-2-{2-[2-(4-Vinylbenzylthio)ethoxy]ethylthio}ethyl succinate

This compound was prepared by procedures analogous to those of Example 2 except substituting the intermediate 2-{2-[2-(4-vinylbenzylthio)ethoxy]ethylthio}ethanol in place of the p-vinylbenzyl alcohol: m.p. of 58°-60° C. Yield of 88% of white solid. Analysis calculated for $C_{19}H_{29}O_5S_2$: C, 57.26, H, 6.50, S, 16.89. Found: C, 57.24, H, 6.87, S, 15.88. $^1$H NMR(CDCl$_3$), 2.65 (m, 10H, C$\underline{CH_2CH_2}$C, $\underline{CH_2}$S—CH$_2$, $\underline{CH_2}$S),
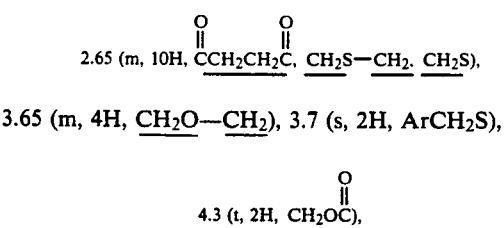

3.65 (m, 4H, $\underline{CH_2}$O—$\underline{CH_2}$), 3.7 (s, 2H, ArCH$_2$S), 4.3 (t, 2H, $\underline{CH_2}$OC), 5.25+5.75 (AB quartet, 2H, CH$_2$=), 6.75 (m, 1H, $\underline{CH}$=), 7.32 (m, 4H, ArH's), 9.6 (broad s, 1H, CO$_2$H).

The series of reactions shown in the following Scheme 1 illustrates the preparation of compounds of this invention comprising one or more p-phenylenemethyleneoxy or p-phenylenemethylenethio groups in the linking group between the carboxy and polymerizable vinyl group. The subsequent examples illustrate the steps of this reaction scheme.

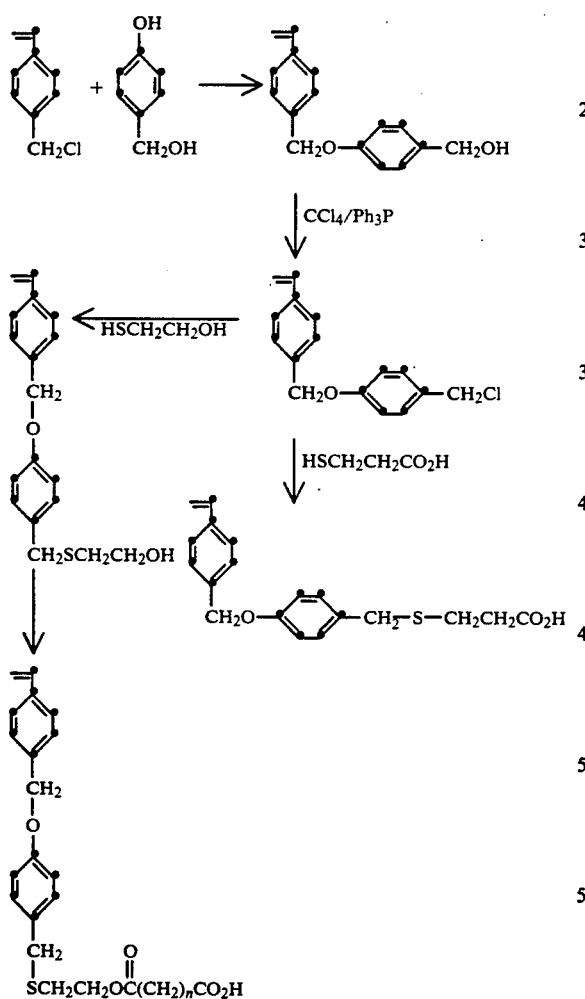

EXAMPLE 16

Preparation of p-Hydroxymethylphenyl 4-vinylbenzyl ether

A mixture of 4-hydroxybenzyl alcohol (56.7 g, 0.459 molar), 85% potassium hydroxide (32.4 g, 0.459 molar) and 2,6-di-tert-butyl-p-cresol (1 g) in ethanol (600 ml) was stirred at room temperature for 30 minutes. To this mixture was added 4-vinylbenzylchloride (70.5 g, 0.459 molar) very rapidly and it was then heated to 80° C. for 6 hours and stirred at ambient temperature overnight. The mixture was cooled, filtered and the solvent reduced to 300 ml by placing on a rotary evaporator. The solution was then placed in the freezer overnight. The next day the product was filtered to give a white solid. This material was recrystallized from methanol/dichloromethane (2/1) to give a white solid: m.p. of 110°–111.5° C. Yield of 77%. Analysis calculated for C$_{16}$H$_{16}$O$_2$: C, 79.97, H, 6.71. Found: C, 79.31, H, 6.69. $^1$H NMR (CDCl$_3$) δ2.55 (broad s, 1H, $\underline{OH}$), 4.5 (s, 2H, $\underline{CH_2}$OH), 5.08 (s, 2H, Ar$\underline{CH_2}$OAr), 5.25+5.75 (AB quartet, 2H, $\underline{CH_2}$=), 6.8 (m, 1H, $\underline{CH}$=), 6.8–7.6 (m, 8H, ArH's).

EXAMPLE 17

Preparation of p-Chloromethylphenyl p-vinylbenzyl ether

A mixture of p-hydroxymethylbenzyl vinylbenzyl ether (39.2 g, 0.16 molar), triphenylphosphine (46.0 g, 0.18 molar), and 2,6-di-tert-butyl-p-cresol (0.5 g) in carbon tetrachloride (550 ml) was heated at reflux for 2 hours and then stirred at ambient temperature overnight. The next day the reaction was filtered and the solvent removed on a rotary evaporator. To the residue was added methanol (300 ml) to precipitate a white solid: m.p. of 110°–112° C. Yield of 83%. Analysis calculated for C$_{16}$H$_{15}$ClO: C, 74.27, H, 5.84. Found: C, 73.15, H, 5.84. $^1$H NMR (CDCl$_3$) δ4.5)s. 2H, CH$_2$Cl), 5.0 (s, 2H, $\underline{CH_2}$O), 5.2+5.75 (AB quartet, 2H, $\underline{CH_2}$=), 6.75 (m, 1H, $\underline{CH}$=),

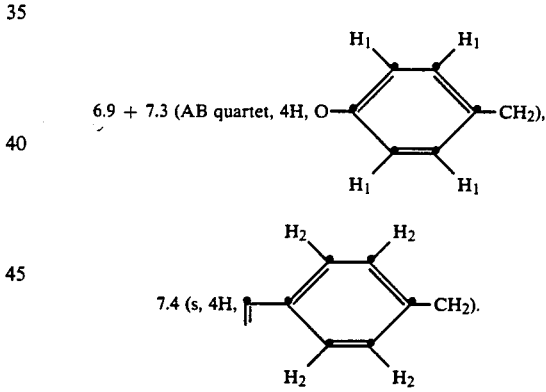

EXAMPLE 18

Preparation of 3-[4-(4-Vinylbenzyloxy)benzylthio]propionic acid

This monomer was prepared by procedures analogous to those of Example 8 except that the p-chloromethylphenyl p-vinylbenzyl ether of Example 17 was substituted for the p-vinylbenzyl chloride: m.p. of 135°–136° C. Yield of 60%. Analysis calculated for C$_{19}$H$_{20}$SO$_3$: C, 69.48, H, 6.14, S, 9.76. Found: C, 68.56, H, 5.99, S, 8.46. 1H NMR (CDCl$_3$) δ2.6 (m, 4H, $\underline{CH_2CH_2}$), 3.7 (s, 2H, Ar$\underline{CH_2}$S), 5.1 (s, 2H, Ar$\underline{CH_2}$O), 5.25+5.75 (AB quartet, 2H, $\underline{CH_2}$=), 6.75 (m, 1H, $\underline{CH}$=), 6.95 + 7.25 (AB quartet, 4H, ArH's of

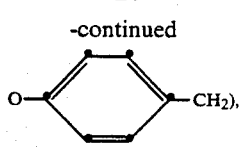

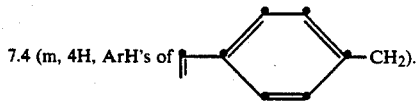

EXAMPLE 19

Preparation of 4-(2-hydroxyethylthiomethyl)phenyl 4-vinylphenyl ether

Variations of the monomer of Example 18 can be prepared as shown in Scheme 1 using the monomer 4-(2-hydroxyethylthiomethyl)phenyl 4-vinylphenyl ether. This was prepared by condensation of the intermediate of Example 17 with 2-mercaptoethanol using procedures analogous to those described for Example 16. Analysis calculated for $C_{18}H_{20}O_2S$: C, 71.97, H, 6.71. Found: C, 71.37, H, 6.52. 1H NMR (CDCl$_3$) δ2.3 (broad s, 1H, C—OH), 2.65 (m, 2H, CH$_2$S), 3.7 (s, 4H, ArCH$_2$S+CH$_2$O), 5.05 (s, 2H, ArCH$_2$O), 5.3+5.8 (AB quartet, 2H, CH$_2$=), 6.75 (m, 1H, CH=),

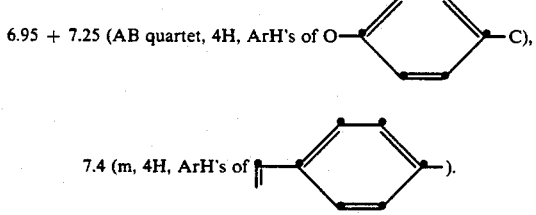

EXAMPLES 20-37

Preparation of Various Copolymers

Several copolymers of this invention were prepared as described below. The procedure for preparing Example 20 is given in detail, but the others are similarly prepared except where noted.

The copolymers prepared are as follows:

EXAMPLE 20
Poly[styrene-co-mono-m and p-(60:40)-vinylbenzyl glutarate] (97.84:2.16 molar ratio).

EXAMPLE 21
Poly{styrene-co-mono-2-[m and p-(60:40)-vinylbenzylthio]ethyl glutarate} (98.3:1.7 molar ratio).

EXAMPLE 22
Poly(styrene-co-mono-p-vinylbenzyl glutarate) (97.84:2.16 molar ratio).

EXAMPLE 23
Poly[styrene-co-mono-2-(p-vinylbenzylthio)ethyl glutarate] (98.3:1.7 molar ratio).

EXAMPLE 24
Poly[styrene-co-3-(p-vinylbenzylthio)propionic acid] (97.6:2.4 molar ratio).

EXAMPLE 25
Poly[styrene-co-3-(p-vinylbenzylthio)propionic acid-co-2-hydroxyethyl acrylate] (92.6:2.4:5.0 molar ratio).

EXAMPLE 26
Poly[styrene-co-4-(4-carboxybutyramido)styrene] (97.7:2.3 molar ratio).

EXAMPLE 27
Poly[styrene-co-4-(4-carboxybutyramidomethyl)styrene] (97.83:2.17 molar ratio).

EXAMPLE 28
Poly{styrene-co-mono-2-[N-methyl-N-(4-vinylbenzyl)amino]ethyl glutarate} (98.24:1.76 molar ratio).

EXAMPLE 29
Poly[styrene-co-3-(p-vinylbenzylthio)propionic acid] (97.59:2.41 molar ratio).

EXAMPLE 30
Poly{styrene-co-4-[2-(4-carboxybutyramido)ethylthiomethyl]styrene} (98.25/1.75 molar ratio).

EXAMPLE 31
Poly{styrene-co-4-[2-(carboxymethoxyacetamido)ethylthiomethyl]styrene} (96.9:3.1 molar ratio).

EXAMPLE 32
Poly{styrene-co-4-[2-(carboxymethylthioacetamido)ethylthiomethyl]styrene} (98.17:1.83 molar ratio).

EXAMPLE 33
Poly[styrene-co-mono-2-(4-vinylbenzylthio)ethyl succinate] (98.17:1.83 molar ratio).

EXAMPLE 34
Poly{styrene-co-4-[2-(carboxymethoxyacetoxy)ethylthiomethyl]styrene} (98.26:1.74 molar ratio).

EXAMPLE 35
Poly(styrene-co-mono-4-vinylbenzyl succinate) (97.71:2.29 molar ratio).

EXAMPLE 36
Poly[styrene-co-2-(4-vinylbenzylthio)succinic acid] (97.98:2.02 molar ratio).

EXAMPLE 37
Poly{{styrene-co-mono-2-{2-[2-(4-vinylbenzylthio)ethoxy]ethylthio}ethyl succinate}} (98.64:1.36 molar ratio).

The polymers of Examples 26, 28, 29 and 31-33 were prepared in particulate form but some coagulation was present. However, the coagulation problems can be overcome by using sufficient surfactant in the polymerization process (the preferred process described below is carried out in the absence of surfactant).

Controls

Several copolymers outside the scope of this invention were prepared using the procedure described below. The following results were found:

An attempt was made to prepare poly(styrene-co-2-acrylamido-2-hydroxyacetic acid) (96.75:3.25 molar ratio in water as a latex), but the particles coagulated severely. Only about 13.9% of theoretical carboxylic acid monomer was incorporated into the copolymer because the 2-acrylamido-2-hydroxyacetic acid is not readily soluble in styrene, and more importantly, because this monomer and its homopolymer are soluble in water.

Similar results were obtained when it was attempted to prepare latices of poly(styrene-co-3-acrylamido-3-methylbutanoic acid) (96.9:3.1 molar ratio), and poly(styrene-co-acryloyloxypropionic acid) (90:10 molar ratio). These copolymers are not readily prepared as latices because the second monomers are too water-soluble and thus, are not soluble in styrene, and more importantly, because the monomers and their homopolymers are soluble in water.

TABLE I

| Example | % Solid | Particle Size (μm) | Carboxy Content* | Stability** |
|---|---|---|---|---|
| 20 | 13.2 | 1.3 | 3.07 | good |
| 22 | 13.6 | 1.5 | 3.37 | fair |
| 21 | 13.6 | 1.5 | 2.39 | good |
| 23 | 15.6 | 1.1 | 3.45 | good |
| 29 | 16.2 | 1.4 | 5.17 | good |
| 33 | 13.8 | 1.2 | 4.59 | fair |
| 34 | 10.6 | 0.8 | — | fair |
| 35 | 11.4 | 1.2 | 4.74 | fair |

*Weight % determined by titration.
**Descriptive of the amount of coagulum. Those having poor stability without surfactant could be stabilized with the use of a surfactant.

The preparatory procedure (specifically for Example 20 ) was as follows:

A suitable three-neck flask (1365 ml) completely filled with water was used as the reaction vessel. At a reaction temperature of 80° C., three streams of reactants were simultaneously pumped into the flask:

Stream 1 contained styrene (839.39 g), m and p-(60:40)-vinylbenzyl glutarate (48.61 g) and 1-dodecanethiol (8.84 g).

Stream 2 contained ammonium persulfate (17.67 g) in distilled water (1661.96 g).

Stream 3 contained sodium bisulfite (8.84 g) in distilled water (1661.96 g).

The rates of pumping the streams were: 2.44 ml/min for Stream 1, 4.21 ml/min for Stream 2 and 4.31 ml/min for Stream 3. The overflow fluid from the vessel was discarded as waste. After an addition time of 360 minutes, the reaction was stopped, yielding 1210 g at 19.2% solids. The resulting polymer latex was dialyzed for 5 days to yield a purified latex at 13.2% solids (average particle size of 1.3 μm). Titration of the latex for carboxyl-containing monomer showed 0.133 milliequivalents/g (3.07%) of the copolymer. Since the monomer was only 76.7% pure, this level of acid corresponds to a 86.7% level of incorporation of the monomer into the copolymer. Similar results were obtained for the copolymers of Examples 21–37.

EXAMPLE 38

Water Solubility Comparisons of Monomers

The water-solubility of several monomers of this invention were compared to that of two monomers outside the scope of this invention. Solubility in an ammonium hydroxide solution (1%) was also determined. The monomers were added at 2.5%. Table II shows the monomers tested and the results obtained. The Control monomers are not within the scope of the present invention. One monomer, Control A was insoluble in water and ammonium hydroxide solution. However, it was not efficiently incorporated into copolymer (see Example 39 below).

TABLE II

| Monomer | Water Solubility* | NH₄OH Solubility* |
|---|---|---|
| Control A | No | No |
| Control B | Yes | Yes |
| Control C | Yes | Yes |
| Example 1 | No | No |
| Example 7 | No | No |

*Solubility at 24° C.
Control A: 2-methacryloyloxyethyl glutarate
Control B: Methacryloylpenta(oxyethylene) glutarate
Control C: Methacryloyldeca(oxyethylene) glutarate

EXAMPLE 39

Polymerization Comparisons

This example compares several polymers of this invention with polymers outside the scope of this invention in the amount of water-soluble comonomers incorporated during emulsion polymerization.

During emulsion polymerization of a mixture of monomers, some of which are generally water-soluble, a portion of the water-soluble monomers form an undesired water-soluble homopolymer in the aqueous phase. It is desired to reduce this portion as much as possible to render the polymerization process more efficient and to get as much of the available water-soluble monomers into the polymeric particles as possible (preferably over 80%).

The polymers compared in this example were prepared using the preparation described above (Example 20). Table III below lists the polymers, the percent of water-soluble monomer incorporated therein and the amount of solution (water-soluble) polymer generated. It is apparent that the polymers of the present invention provided more efficient incorporation of the monomers and were generated with less solution polymer.

TABLE III

| Polymer | % Water Soluble Monomer Incorporated | Solution Polymer (milliequivalents/g) |
|---|---|---|
| Control A | 34 | 0.020 |
| Control B | 34 | 0.016 |
| Control C | 72 | NA* |
| Control D | 42 | 0.013 |
| Control E | 52 | 0.038 |
| Example 20 | 94 | 0.010 |
| Example 21 | 81 | 0.007 |

*Not available
Control A: Poly[styrene-co-methacryloyldeca(oxyethylene)glutarate] (99.2:0.8 molar ratio)
Control B: Poly[styrene-co-methacryloylpenta(oxyethylene)glutarate] (98.7:1.3 molar ratio)
Control C: poly(styrene-co-mono-2-methacryloyloxyethyl glutarate) (97.84:2.16 molar ratio)
Control D: poly[styrene-co-mono-methacryloylpenta-(oxyethylene)phthalate] (98.81:1.19 molar ratio)
Control E: poly[styrene-co-mono-methacryloyldeca-oxyethylene)phthalate] (99.19:0.81 molar ratio)

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A polymer comprising recurring units derived from:
   (a) from 80 to about 99.8 mole percent of one or more ethylenically unsaturated polymerizable, non-crosslinkable, vinyl aromatic monomers which provide hydrophobicity to said polymer,
   (b) from about 0.2 to 20 mole percent of one or more ethylenically unsaturated polymerizable monomers represented by the structure:

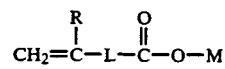

wherein:

R is hydrogen, halo or alkyl of 1 to 3 carbon atoms,
M is hydrogen, an alkali metal ion or an ammonium ion, and
L is a linking group having from 8 to 50 atoms in its linking chain, and comprises two or more divalent hydrocarbon groups connected or terminated with one or more nitrogen, oxygen or sulfur atoms, or with one or more groups containing said atoms in the linking chain, provided L has at least one arylene which is not directly connected to the terminal

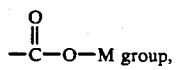
—C—O—M group, and further provided that none of said hydrocarbon groups has non-aromatic unsaturation, and
(c) from 0 to about 15 mole percent of one or more additional ethylenically unsaturated polymerizable monomers other than those identified in categories (a) and (b) above.

2. The polymer of claim 1 wherein R is hydrogen or methyl, M is hydrogen or an alkali metal ion, and said hydrocarbon groups are selected from the group consisting of alkylene, arylene, alkylenearylene and arylenealkylene which are connected or terminated with an oxy, thio, imino (—NR$^1$—), carbonyloxy (—COO—), carbonylimino (—CONR$^1$—), ureylene (—NR$^1$CONR$^1$—) or sulfonylimino (—SO$_2$NR$^1$—) group, wherein each R$^1$ is independently hydrogen, alkyl having 1 to 10 carbon atoms, cycloalkyl having 4 to 10 carbon atoms or aryl having 6 to 14 carbon atoms.

3. The polymer of claim 2 wherein L is p-phenylenemethyleneoxycarbonyltrimethylene, carbonyloxy-p-phenyleneurylenepentamethylene, p-phenylenemethylenethioethyleneoxycarbonyltrimethylene, p-phenylenemethyleneiminocarbonyltrimethylene, p-phenylenemethyleneiminocarbonyltrimethylene, p-phenylene(methyl)iminoethyleneoxycarbonyltrimethylene, p-phenylenemethylenethioethylene, p-phenylenemethylenethioethyleneiminocarbonylmethyleneoxymethylene, p-phenylenemethylenethioethyleneiminocarbonylmethylenethiomethylene, p-phenylenemethylenethioethyleneiminocarbonyltrimethylene, p-phenylenemethylenethio-1-carboxyethylene, p-phenylenemethylenethio-p-phenylene, p-phenylenemethylenethioethyleneoxyethylenethiomethyleneoxycarbonylethylene, p-phenylenemethyleneoxy-p-phenylenemethylene-thioethylene, p-phenylenemethylenethioethyleneoxy-ethylenethioethyleneoxycarbonylethylene, p-phenylene-methyleneoxy-p-phenylenemethylenethio-p-phenylenemethylenethiotrimethylene and p-phenylenemethylenethioethyleneoxyethylenethioethyleneoxycarbonyl-p-phenylene.

4. The polymer of claim 1 wherein monomer (b) is selected from the group consisting of: mono-m and p-vinylbenzyl glutarate, mono-p-vinylbenzyl glutarate, 4-(4-carboxybutyramido)styrene, mono-2-(p-vinylbenzylthio)ethyl glutarate, mono-2-(m and p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]-styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio]benzylthio}butyric acid.

5. The polymer of claim 1 wherein monomer (a) is selected from the group consisting of styrene, 4-vinyltoluene, α-methylstyrene, 2,5-dimethylstyrene, 4-t-butylstyrene, 2-chlorostyrene, m and p-chloromethylstyrene, p-hydroxystyrene, 2,5-dimethoxystyrene, 3,4-dimethoxystyrene and 3,4-methylenedioxystyrene.

6. The polymer of claim 1 selected from the group consisting of:
poly[styrene-co-2-(4-vinylbenzylthio)succinic acid],
poly[styrene-co-2-(4-vinylbenzylthio)benzoic acid],
poly{{styrene-co-mono-2-{2-[2-(4-vinylbenzylthio)ethoxy]ethylthio}ethyl succinate}},
poly(styrene-co-mono-m and p-(60:40)-vinylbenzyl glutarate),
poly[styrene-co-mono-2-(m and p-vinylbenzylthio)ethyl glutarate],
poly[styrene-co-3-(p-vinylbenzylthio)propionic acid],
poly[styrene-co-mono-2-(4-vinylbenzylthio)ethyl succinate],
poly{styrene-co-4-[2-(carboxymethoxyacetoxy)ethylthiomethyl]styrene},
poly(styrene-co-mono-4-vinylbenzyl succinate),
poly[styrene-co-3-p-(vinylbenzylthio)propionic acid], and
poly[styrene-co-3-(p-vinylbenzylthio)propionic acid-co-2-hydroxyethyl acrylate].

7. An aqueous latex composition comprising particles having, at least on the outer surface thereof, a water-insoluble polymer comprising recurring units derived from:
(a) from 80 to about 99.8 mole percent of one or more ethylenically unsaturated polymerizable, non-crosslinkable, vinyl aromatic monomers which provide hydrophobicity to said polymer,
(b) from about 0.2 to about 20 mole percent of one or more ethylenically unsaturated polymerizable monomers represented by the structure:

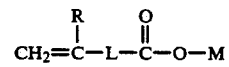

$$CH_2=C-L-C-O-M$$

wherein:
R is hydrogen, halo or alkyl of 1 to 3 carbon atoms,
M is hydrogen, an alkali metal ion or an ammonium ion, and
L is a linking group having from 8 to 50 atoms in its linking chain, and comprises two or more divalent hydrocarbon groups connected or terminated with one or more nitrogen, oxygen or sulfur atoms, or with one or more groups containing said atoms in the linking chain, provided L has at least one arylene which is not directly connected to the terminal

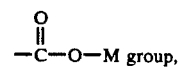
—C—O—M group, and further provided that none of said hydrocarbon groups has non-aromatic unsaturation, and (c) from 0 to about 15 mole percent of one or more additional ethylenically unsaturated polymerizable monomers other than those identified in categories (a) and (b) above, the particles being present at from about 0.5 to about 50 weight percent of the composition.

8. The composition of claim 7 wherein R is hydrogen or methyl, M is hydrogen or an alkali metal ion, and said hydrocarbon groups are selected from the group consisting of alkylene, arylene, alkylenearylene and arylenealkylene which are connected or terminated with an oxy, thio, imino (—$NR^1$—), carbonyloxy (—COO—), carbonylimino (—$CONR^1$—), ureylene (—$NR^1CONR^1$—) or sulfonylimino (—$SO_2NR^1$—) group, wherein each $R^1$ is independently hydrogen, alkyl having 1 to 10 carbon atoms, cycloalkyl having 4 to 10 carbon atoms or aryl having 6 to 14 carbon atoms.

9. The composition of claim 8 wherein monomer (b) is selected from the group consisting of: mono-m and p-vinylbenzyl glutarate, mono-p-vinylbenzyl glutarate, 4-(4-carboxybutyramido)styrene, mono-2-(p-vinylbenzylthio)ethyl glutarate, mono-2-(m and p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)-benzylthio]propionic acid and 4-{4-[4-(4-vinyl-benzyloxy)benzylthio]benzylthio}butyric acid.

10. The composition of claim 7 wherein monomer (a) is selected from the group consisting of: styrene, 4-vinyltoluene, α-methylstyrene, 2,5-dimethylstyrene, 4-t-butylstyrene, 2-chlorostyrene, m and p-chloromethylstyrene, p-hydroxystyrene, 2,5-dimethoxystyrene, 3,4-dimethoxystyrene and 3,4-methylenedioxystyrene.

11. The composition of claim 7 which is substantially free of surfactants and colloidal dispersing agents.

12. The composition of claim 7 wherein said polymeric particles have an average diameter of from about 0.01 to about 20 μm.

* * * * *